(12) United States Patent
Soares et al.

(10) Patent No.: US 9,872,972 B2
(45) Date of Patent: Jan. 23, 2018

(54) METHODS AND DEVICES FOR LOCATING AND ADJUSTING AN IMPLANTABLE VALVE

(71) Applicant: DePuy Synthes Products, LLC, Raynham, MA (US)

(72) Inventors: Brian Soares, Norton, MA (US); Alyssa Trigger, South Boston, MA (US); Alan Dextradeur, Franklin, MA (US)

(73) Assignee: Integra LifeSciences Switzerland SARL, Raynham, MA (US)

( * ) Notice: Subject to any disclaimer, the term of this patent is extended or adjusted under 35 U.S.C. 154(b) by 632 days.

(21) Appl. No.: 14/477,372

(22) Filed: Sep. 4, 2014

(65) Prior Publication Data
US 2016/0067463 A1     Mar. 10, 2016

(51) Int. Cl.
  *A61M 5/00*     (2006.01)
  *A61M 27/00*    (2006.01)

(52) U.S. Cl.
  CPC ..... *A61M 27/006* (2013.01); *A61M 2027/004* (2013.01); *A61M 2209/01* (2013.01); *A61M 2209/04* (2013.01)

(58) Field of Classification Search
  CPC .......... A61M 27/006; A61M 2027/004; A61M 2209/01; A61M 2209/04
  See application file for complete search history.

(56) References Cited

U.S. PATENT DOCUMENTS

| 4,676,772 A * | 6/1987 | Hoover ............... A61M 27/006 116/204 |
| 5,643,194 A | 7/1997 | Negre |
| 7,921,571 B2 | 4/2011 | Moureaux et al. |
| 8,038,641 B2 | 10/2011 | Soares et al. |
| 8,241,240 B2 | 8/2012 | Murphy |
| 2002/0022793 A1* | 2/2002 | Bertrand ............ A61M 27/006 604/9 |
| 2013/0102951 A1 | 4/2013 | Swoboda et al. |

FOREIGN PATENT DOCUMENTS

| EP | 2236169 A1 | 10/2010 |
| EP | 2420284 A2 | 2/2012 |

OTHER PUBLICATIONS

U.S. Appl. No. 14/040,865, filed Sep. 30, 2013.
European Search Report for Application No. 15183705.1 dated Jan. 26, 2016 (9 pages).

* cited by examiner

*Primary Examiner* — Philip R Wiest
(74) *Attorney, Agent, or Firm* — Mintz Levin Cohn Ferris Glovsky and Popeo, P.C.

(57) ABSTRACT

Methods and devices are provided that allow a physician to consistently and reliably locate an implantable, magnetically settable valve (valve) and to determine and/or change (adjust) a setting of the valve from a current setting to a target setting without interference from the valve and/or patient's skin. In particular, various locator tools are provided that include a housing having a deck extending thereacross that is formed at least in part of a material which is moveable to accommodate a protrusion of a hydrocephalus valve beneath skin.

20 Claims, 10 Drawing Sheets

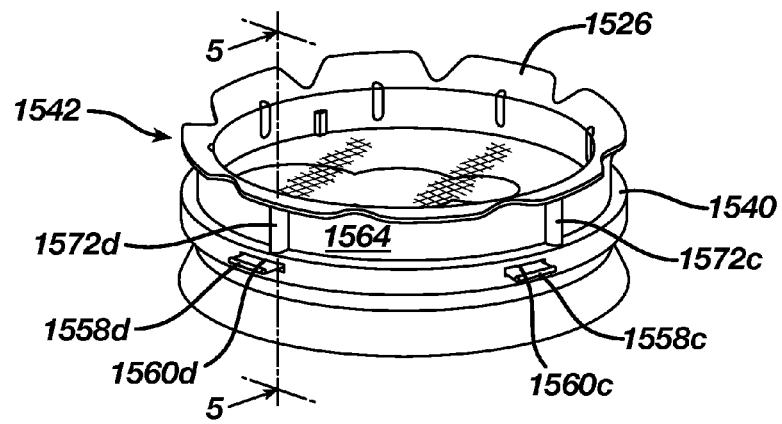
FIG. 5B
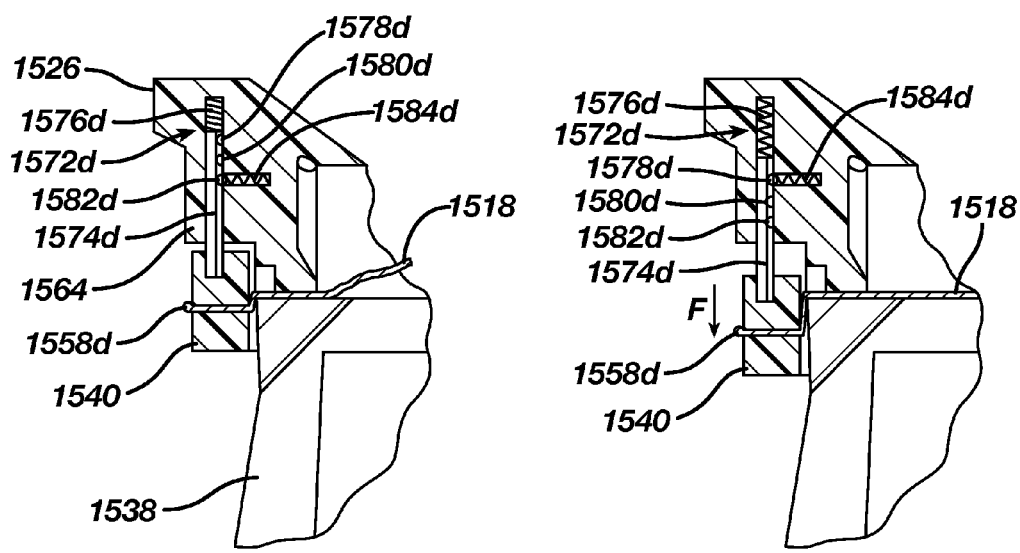
FIG. 5C  FIG. 5D

METHODS AND DEVICES FOR LOCATING AND ADJUSTING AN IMPLANTABLE VALVE

FIELD

The present inventions relates generally to extracorporeal tools and methods for locating adjustable valves used for cerebrospinal fluid drainage.

BACKGROUND

Hydrocephalus is a neurological condition caused by the abnormal accumulation of cerebrospinal fluid (CSF) within the ventricles, or cavities, of the brain. Hydrocephalus, which can affect infants, children and adults, arises when the normal drainage of CSF in the brain is blocked in some way. Such blockage can be caused by a number of factors, including, for example, genetic predisposition, intraventricular or intracranial hemorrhage, infections such as meningitis, or head trauma. Blockage of the flow of CSF consequently creates an imbalance between the rate at which CSF is produced by the ventricular system and the rate at which CSF is absorbed into the bloodstream. This imbalance increases pressure on the brain and causes the ventricles to enlarge. Left untreated, hydrocephalus can result in serious medical conditions, including subdural hematoma, compression of the brain tissue, and impaired blood flow.

Hydrocephalus is most often treated by surgically inserting a shunt system to divert the flow of CSF from the ventricle to another area of the body, such as the right atrium, the peritoneum, or other locations in the body where CSF can be absorbed as part of the circulatory system. Various shunt systems have been developed for the treatment of hydrocephalus. Typically, shunt systems include a ventricular catheter that extends into the ventricle of a patient, a shunt valve for controlling the flow rate of fluid draining from the ventricle, and a drainage catheter extending from the shunt valve into another area of the body. Typically, the shunt valve is palpatable by the physician through the patient's skin after implantation.

It is important to be able to externally read or verify the setting of the valve in conjunction with adjusting its characteristics. With some adjustable valves, x-ray images are used to determine the current setting of the valve, before and after adjustment. With other adjustable valves, the orientation of a rotor in the valve can be read magnetically, using a magnetic compass-like device positioned above the valve, outside the skin of the patient. Such a device is known as an indicator tool. Some valve adjustment systems utilize a separate adjuster tool for adjusting the characteristics of the valve. Both the adjuster tool and the indicator tool can be used in conjunction with a locator tool. The locator tool is designed to be placed over the valve site to indicate the location and orientation of the valve under the skin, and subsequently to maintain the locator tool in position relative to the established position and orientation of the valve. When the position has been established, the adjuster and indicator tools can be engaged within the locator tool to perform their respective functions.

Although tools and methods exist for adjusting CSF shunt valve settings, as do other tools and methods for reading a valve setting, some have difficulty performing their function if the underlying valve protrudes too far from the skull into the locator tool. This may happen due to swelling or in instances where the patient has a thick or thin scalp, or a smaller or larger skull than is typical. In these instances, the valve can interfere with the placement and operation of the adjustor and/or indicator tools. Parallel placement of the locator to the implanted valve whilst in closest proximity to the implanted valve whilst permitting complete engagement between the locator and the indicator and adjustment tools enables successful operation of these tools.

Accordingly, a need exists for tools that enable the locator to be held by the user against the skin in a position generally parallel to the implanted valve, while preventing interference between the skin/valve and the adjustor and indicator tools.

SUMMARY

Various methods, systems, and devices are provided herein for locating, reading, and adjusting an implanted subdermal valve. In one embodiment, a locator tool for locating a valve implanted beneath skin and includes an annular base member having a proximal end and a distal end that is configured to be placed on a skin surface above a valve implanted beneath the skin surface, and a deck supported across the base member and having at least a portion formed of a material through which at least one of visual and tactile access is obtainable. The material can be movable to accommodate a valve protrusion in a skin surface on which the base member is configured to be placed.

The material can have various configurations and include various features. For example, in one embodiment at least a portion of the material is transparent to allow a valve to be seen therethrough. The material can include features such as one or more holes for marking at least one of a location and an orientation of a valve. In certain aspects, the material can be an elastic material which is movable by deforming around a protrusion of skin. In other embodiments, the material of the deck can be a non-elastic material. The non-elastic material can be movable between a taut configuration and an untaut configuration in which the material can move around a protrusion of skin. By way of example, an adjustment mechanism can be provided for adjusting a tautness of the material.

In other embodiments, the base member can have a central opening extending therethrough and defining a central axis, and the material can be held by an annular support member mounted to move relative to the base member along the central axis. The base member and the annular support member can include corresponding slots and protrusions to allow relative movement between the base member and the support member. The tool can also include a mechanism to selectively fix the support member relative to the base member. The tool can include other features such as a biasing element for biasing the support member toward a proximal end of the base member.

In another embodiment, the deck can include a rigid portion extending across the base member and having a valve cut-out formed therein. The material can extend across the valve cut-out. The material can be movable toward and away from the rigid portion.

In yet another embodiment, a kit for locating and adjusting a valve implanted beneath a skin surface is provided and includes a locator tool, an indicator tool, and an adjustment tool. The locator tool can have an annular base member configured to be placed on a skin surface above a valve implanted beneath the skin surface, and a deck supported across the base member and having at least a portion formed of a material through which at least one of visual and tactile access is obtainable. The material can be movable to accommodate a valve protrusion in a skin surface on which the base member is configured to be placed. The indicator tool can be removably disposable within the locator tool and it can be configured to indicate a setting of a valve, and the adjustment tool can also be removably disposable within the locator tool and it can be configured to adjust a setting of a valve.

The deck of the locator tool can have various configurations, including those discussed above. For example, the deck can include a rigid portion having a valve cut-out formed therein, and wherein the material extends across the valve cut-out. At least a portion of the deck of the locator tool can form a platform on which the indicator tool and the adjustment tool seat against when disposed therein.

Methods for locating a valve implanted beneath skin are also provided and in one embodiment the method includes positioning a base member of a locator tool on a skin surface above a valve implanted beneath the skin surface. At least a portion of a deck of the locator tool supported across the base member moves relative to the base member to accommodate a protrusion of skin around the valve. In one embodiment, the portion of the deck that moves can be a material that moves relative to the base member to accommodate a protrusion of skin around the valve. The method can further include adjusting a height of the material relative to the base member and the skin surface. In another embodiment, the method can further include moving the material from an untaut positon to a taught position. The method can include marking skin beneath the deck through holes in the deck to indicate features of a valve, and/or placing at least one of an indicator and a valve adjustment tool on the deck.

BRIEF DESCRIPTION OF THE DRAWINGS

This invention will be more fully understood from the following detailed description taken in conjunction with the accompanying drawings, in which:

FIG. 5B is a side perspective view of the locator tool of FIG. 5A in a partially assembled configuration;

FIG. 5C is an enlarged side view of a mating connection of the locator tool shown in FIG. 5B taken across line 5, showing the locator tool in a fully assembled configuration and showing a deck of the locator tool in an unbiased configuration;

FIG. 5D is an enlarged side view of a mating connection of the locator tool shown in FIG. 5B taken across line 5, showing the locator tool in a fully assembled configuration and showing a deck of the locator tool in a biased configuration.

DETAILED DESCRIPTION

Figure 1A:
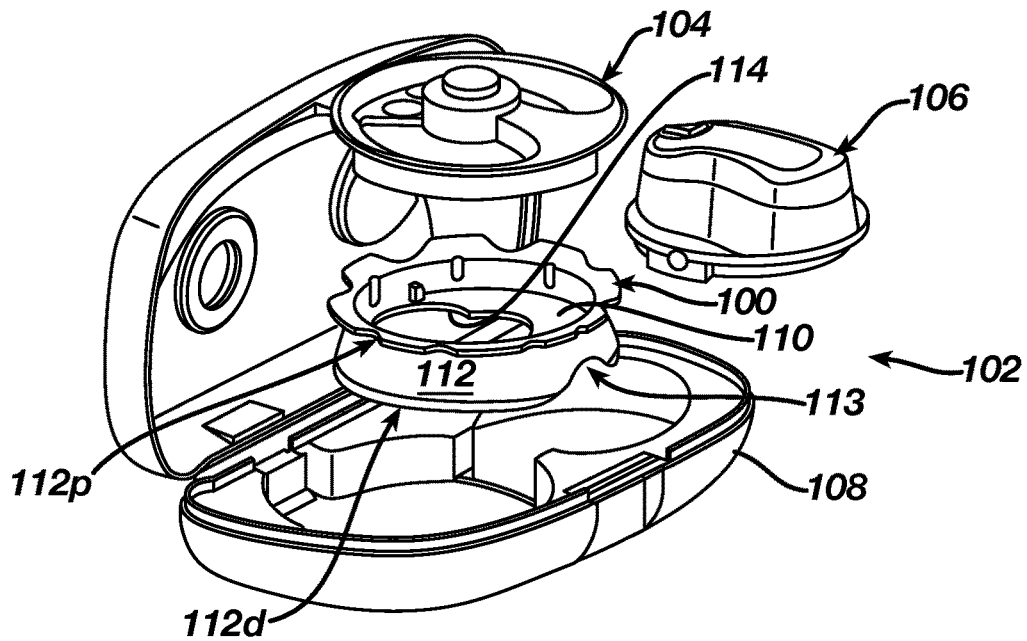
FIG. 1A is a perspective view of one embodiment of a kit that includes a locator tool, an indicator tool, an adjustment tool, and a case for holding the tools.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, methods and devices are provided that allow a physician to consistently and reliably locate an implantable, magnetically settable valve (valve) and to determine and/or change (adjust) a setting of the valve from a current setting to a target setting without interference from the valve and/or patient's skin. In particular, various locator tools are provided that include a housing having a deck extending thereacross that is formed at least in part of a material which is moveable to accommodate a protrusion of a hydrocephalus valve beneath skin. Such a configuration allows for visual and/or tactile access to an implanted valve. The locator tools can be used with indicator and/or adjustment tools to be seated on the deck of the locator tool and positioned in close proximity to the valve, while being maintained in a parallel orientation with respect to the deck of the locator tool.

While the devices and methods disclosed herein can be used with various types of valves, in one embodiment the valve can be implanted under a skin surface, e.g., a scalp, of a patient having hydrocephalus. The valve can located and adjusted from the outside (above) the patient's skin to control, via its setting, at least one of CSF drainage flow and pressure. Other tools and methods for extracorporeally reading and adjusting a hydrocephalus valve are disclosed in U.S. Pat. No. 8,038,641 entitled "Tools and Methods for Programming an Implantable Valve," and in U.S. patent application Ser. No. 14/040,865 filed on Sep. 30, 2013 and entitled "Adjustable Height Hydrocephalus Valve Location Device," each of which is hereby incorporated by reference in its entirety.

Throughout the following, "lower" or "bottom" or "beneath" or "distal" etc. are used to indicate a portion of a tool which is intended to be placed nearer to a patient's skin, whilst "above" and "upper" and "top" and "proximal" etc. are used to indicate a part of a tool which will be closest to the user of the tool and farther from the patient's skin than lower parts of the tool. An imaginary axis running in a proximal-distal direction, substantially perpendicular to the deck, indicates generally a central axis of the locator tools disclosed herein.

FIG. 1A illustrates one embodiment of a tool set or kit 102 that includes a locator tool 100 for locating an implanted valve, an indicator tool 104 for indicating a current setting of the valve, and an adjustment tool 106 for adjusting the setting of the valve. The indicator tool 104 and the adjustment tool 106 are each configured to be seated on and optionally received within the locator tool 100 to measure/adjust the setting of a valve located by the locator tool. While the indicator tool 104 and the adjustment tool 106 are not described in detail herein, a person skilled in the art will appreciate that various indicator and adjustment tools can be used in connection with the various locator tools described herein, including the tools described in the references cited above. FIG. 1A further illustrates a case 108 for carrying the various components of the kit.

Figure 1B:
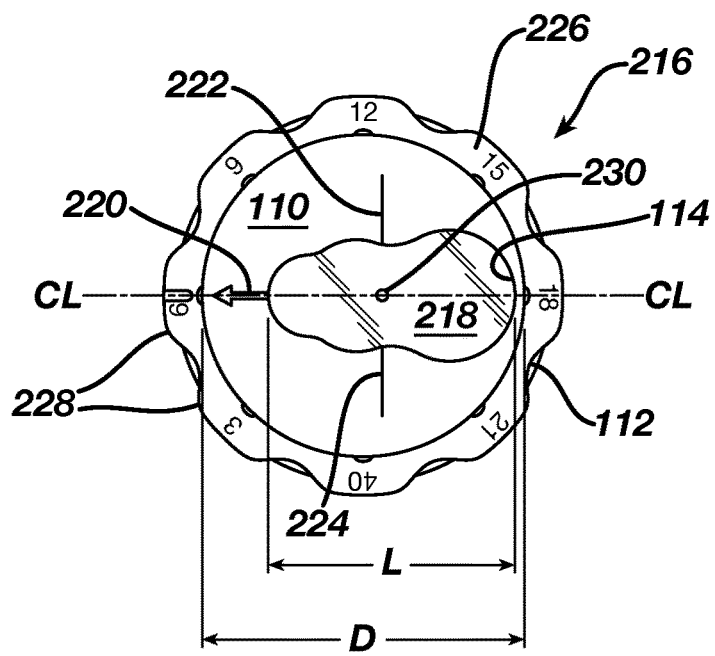
FIG. 1B is a top view of the locator tool of FIG. 1A showing a flexible member positioned beneath a rigid deck having a valve cut-out formed therein.

The locator tool 100 of FIG. 1A is shown in more detail in FIG. 1B, and generally includes a rigid, generally annular wall or housing 112 defining an opening and having a diameter D. A deck 110 extends across the opening of the housing 112, e.g., substantially perpendicular to the housing 112. While the deck 110 can extend in a plane that is positioned at any height with respect to the housing 112, in the illustrated embodiment (as shown in FIG. 1A) the deck 110 is positioned across a mid-portion of the housing 112 such that the housing 112 and the deck 110 define a proximal cylindrical cavity for seating the indicator tool 104 or the adjustment tool 106, as well as a distal cylindrical cavity (not shown) for receiving the implanted valve (including the skin overlying the valve). The depth of the proximal cavity is generally defined by the distance from the deck 110 to the proximal-most edge 112p of the housing 112, and the depth of the distal cavity is generally defined by the distance from the deck 110 to the distal-most edge 112d of the housing 112.

As shown in FIG. 1A, the distal end of the housing 112 can also include first and second catheter cut-outs (only one cut-out 113 is shown) formed in opposed sides thereof for allowing the housing 112 to be seated over a valve with the catheters of the valve extending through the cut-outs.

As shown in FIG. 1B, the housing 112 can also include a rim 226 extending radially outward from the proximal-most edge 112p. The rim 226 can form an outer, annular region of the upper surface of the locator tool 100, and it can have a number of tabs 228, two of which are labeled. There are a total of eight tabs on the illustrated rim 226, although this is only an example and there could be more or fewer, although the number is usually chosen to correspond to the number of valve settings. In this example, each tab bears a number, each of which corresponds to a possible pressure setting of a valve. These numbers can be referenced during use of an adjustment tool placed in the locator tool 100, as discussed below.

The deck 110 which extends across the opening of the housing 112 of the locator tool can have a variety of configurations, and it can be formed from one or more portions or layers. In the illustrated embodiment, the deck 110 is in the form of a rigid surface having a valve cut-out 114 formed therein. A material or membrane 218 is disposed beneath the rigid surface and extends across the valve-cut out 114. The deck 110 and/or the underlying membrane 218 can be fixedly and immovably coupled to the housing 112, e.g. attached with an adhesive, welded, using fasteners, or using other known techniques. In other embodiments, one or more of the layers or portions can be movably coupled to the housing, exemplary embodiments of which will be discussed in more detail below.

The rigid portion of the deck 110 can be generally annular and can occupy the entire opening in the housing 112, such that the outer perimeter of the deck 110 is mated to the housing 112. The valve cut-out 114 can be formed through the rigid deck 110 to allow a valve to be palpated therethrough. The cut-out 114 may be sized and shaped similarly to the type of valve over which it is placed, such that with the cut-out placed over the valve, the general orientation of the valve is known. For example, in FIG. 1B, the deck 110 has a cut-out 114 which is "snowman"-shaped, i.e. small, medium, and large circles arranged in order of size and having a degree of overlap between the small and the medium circles and the medium and the large circles, which together make a shape having a length greater than a diameter of the large circle (although this is not essential). The dimensions of the cut-out 114 can also vary depending on the dimensions of the underlying valve. In the illustrated embodiment, the cut-out 114 has a length L which is less than the diameter D of the deck 110, in this example approximately three quarters of the diameter D, although this proportion is a non-limiting example. A centerline CL of the cut-out 114 is shown through its length L. The cut-out 114 in this example is positioned offset with its larger end (i.e. the end formed by the large circle) being locator closer to the housing 112 than its smaller end. In other words, it is not centered on the deck 110 with respect to its length, although it is substantially centered with respect to its width. This positioning is exemplary and could be varied. Once placed over the valve, the locator tool 100 can be oriented to align a center axis of the length of the cut-out with the magnetic axis of the valve.

The membrane 218 underlying the rigid deck 110 can also be substantially circular and can have a size that is similar to the size of the rigid deck 110, such that it covers the cross-sectional area of the cylindrical cavity defined by the housing 112. The membrane 218 can be formed from various materials and can have various properties, e.g., it can be transparent, opaque, or variations therebetween, and/or it can be elastic or non-elastic, or variations therebetween. In the illustrated embodiment the membrane 218 is transparent or substantially transparent or translucent in the visible light spectrum so that it has minimal effect on the visibility of the patient's skin. In other words, it allows at least a degree of visual access to the underlying implanted valve. The illustrated membrane 218 is also formed from a material that is elastically deformable so as to allow the membrane 218 to deform around an implanted valve received within the housing 112 of the locator tool 100, and/or to allow a user to move the membrane 218 so as to feel the underlying implanted valve. The material can be chosen such that a valve can be felt through the material, i.e., to allow tactile access. By way of non-limiting example, the material can be silicon or a silicon-based material. The thickness of the membrane can vary, and by way of non-limiting example the membrane can have a thickness that is approximately 1/16 inch. The thickness can also vary throughout the membrane such that the region beneath the cut-out 114 allows for palpation while other surrounding regions may have a different thickness.

The deck 110 (including both the rigid portion and the membrane 218) can include a number of additional features for facilitating positioning and alignment of the locator tool 100 with respect to an implanted valve. As further shown in FIG. 1B, a marking in the form of an arrow 220 is provided on the rigid portion of deck 110 oriented along the centerline CL pointing away from the smaller end of the cut-out 114. The arrow 220 indicates to a physician a direction of fluid flow through the underlying valve, thus facilitating proper alignment of the locator tool 100 with the valve. The illustrated locator tool 100 also includes markings in the form of lines 222, 224 that extend perpendicular to the arrow 220 to provide additional visual alignment features. FIG. 1B further illustrates a hole 230 formed in the membrane 218 through which a patient's skin can be marked to further facilitate positioning and alignment of the locator tool 100 with respect to the valve. In this example, the hole is located on a centerline CL of the cut-out 114, although the location can vary.

Figure 1C:
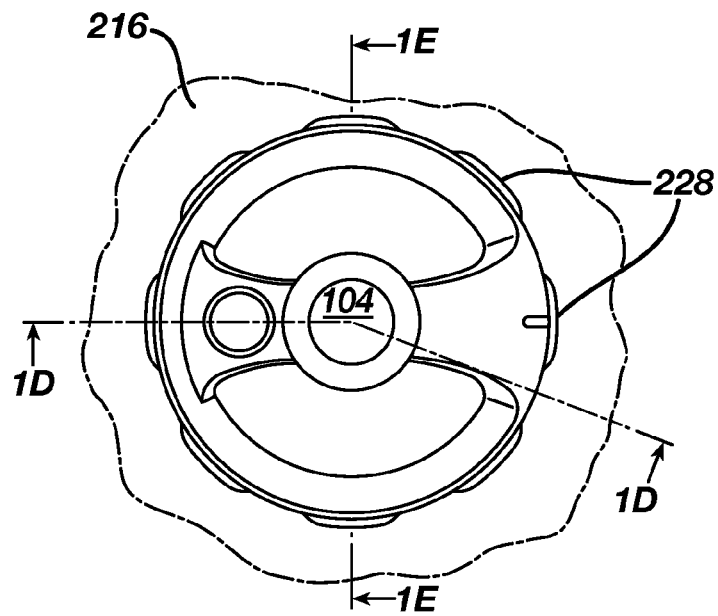
FIG. 1C is a top view of the locator tool of FIG. 1A positioned on a skin surface and having the indicator tool of FIG. 1A seated therein.
Figure 1D:
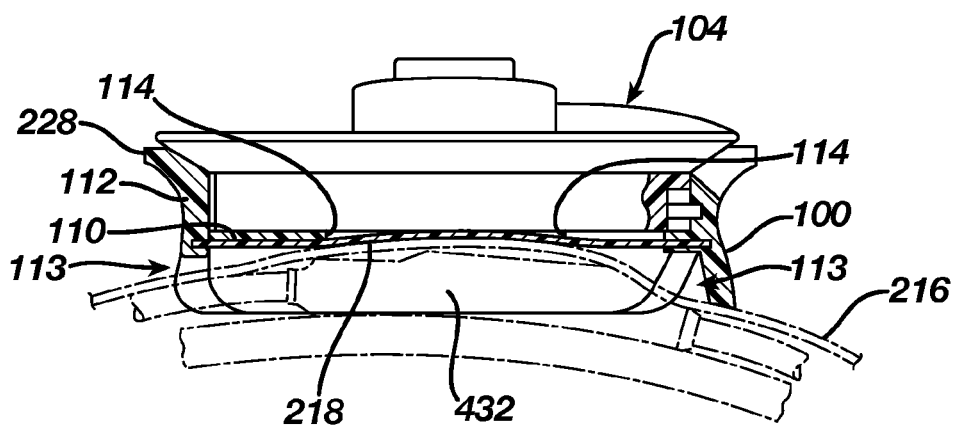
FIG. 1D is a side cross-sectional view of the tools of FIG. 1C taken across line 1D.
Figure 1E:
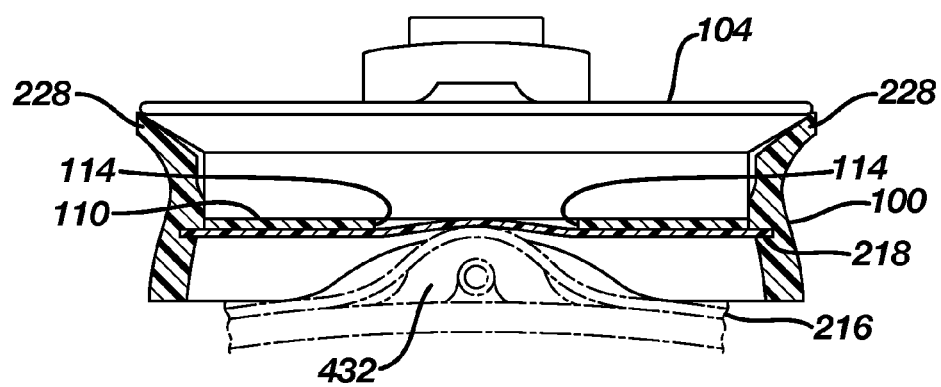
FIG. 1E is another side cross-sectional view of the tools of FIG. 1C taken across line 1E.

FIGS. 1C-1E illustrate the locator tool 100 in use. As shown, the locator tool 100 can be placed on a skin surface 216 having a valve, e.g., a hydrocephalus valve 432 implanted underneath the skin surface 216. The catheter cut-outs 113 can be aligned to extend around the proximal and distal catheters extending from opposite ends of the valve 432, as shown in FIG. 1D. The valve cut-out 114 can be positioned in alignment with the valve 432 by tactile feel or and visual location of the valve through the membrane 218. The directional arrow and other markings can also be used to facilitate alignment. If desired, the skin can be marked through the hole 230.

When the locator tool 100 is positioned on the skin overlying the valve, the membrane 218 can move, e.g., by deforming around a skin protrusion above the valve, and/or as a result of deformation during tactile feel of the underlying valve. FIG. 1D is a partial cross-section through FIG. 1C. It can be seen in FIG. 1D that the membrane 218 has moved into the cut-out 114 to such an extent that it is substantially flush with the deck 110. This movement has occurred to accommodate the protrusion of the skin 216 above the valve 432. In this implementation, the movement has occurred by way of the material of the membrane 218 undergoing deformation, which is possible in view of its flexible nature. This movement may afford greater comfort to the patient than would be experienced if the rigid deck 110 were placed directly on the skin 216 in the region of a valve. This comfort is optimized by the membrane 218 extending across the area enclosed by the housing 112, but the membrane 218 could be smaller if desired. FIG. 1E is also a partial cross-section through FIG. 1C and also shows the deformation of the membrane 218 to accommodate the protrusion of the valve 432 beneath the skin 216. This view is looking on the centerline CL of the valve 432 and the cut-out 114 and it should be noted that the locator tool 100 is disposed in a substantially horizontal orientation (i.e. parallel to the skin 216). Preferably, the locator tool 100 has a height that prevents the valve from passing entirely through the cut-out 114 in the deck so as to avoid interference with the indicator and adjustments tools when seated therein. A person skilled in the art will appreciate that the height can vary, and while not shown the height can optionally be adjustable.

Once the locator tool 100 is properly positioned and in alignment with the valve 432, the indicator and adjustment tools 104, 106 can be placed within the cylindrical cavity or opening of the locator tool 110. The rigid portion of the deck 110 will seat the tools so as to maintain the tools in an orientation substantially perpendicular to the skin surface. As shown, the top surface of the indicator tool 104 is visible, together with the outer extents of the tabs 228 of the locator tool 100. The indicator tool 104 can include a magnet and an actuator that, when depressed, will allow the magnet to align with the magnet in the valve so as to indicate the current setting of the valve. Once determined, the indicator tool 104 can be removed and the adjustment tool 106 can be seated within the locator tool 100 to adjust the setting of the valve. Techniques for using the indicator and adjustment tools 104, 106 are described in more detail in the aforementioned references.

Figure 2:
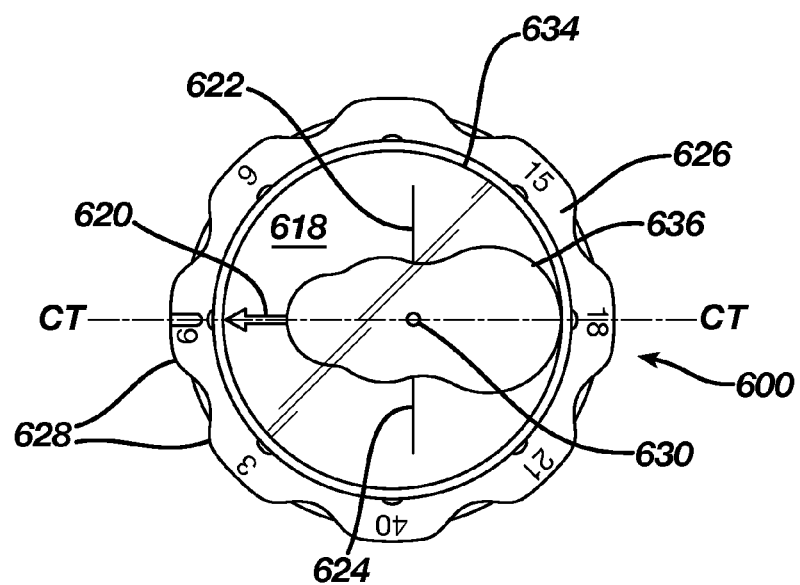
FIG. 2 is a top view of another embodiment of a locator tool having a flexible membrane extending thereacross with markings formed therein for locating an implanted valve.

FIG. 2 illustrates another embodiment of a locator tool 600 that is similar to the locator tool 100 of FIGS. 1A-1E, but that lacks a rigid portion on the deck 110. Instead, the locator tool 600 has an annular ridge 634 extending around an inner surface of the housing a distance from the proximal-most and distal-most ends of the tool 600. The annular ridge 634 can be rigid and can be attached to or integrally formed on the inner wall of the housing. The ridge 634 defines a proximal-facing surface upon which the adjustment and indicator tools can rest.

The locator tool 600 has a membrane 618, which may be similar to the membrane 218 of FIGS. 1A-1E in size, shape, and material properties. The membrane 618 can be attached to any portion of the housing, although the illustrated embodiment shows the membrane seated on the proximal-facing surface of the ridge 634. The membrane 618 can be fixedly attached to the ridge 634, for example by permanent adhesive or other permanent fixing. It can alternatively be removably seated on the ridge 634 using a removable attachment mechanism, such as fasteners etc. The membrane 618 can also include a hole 630, positioned similarly to the hole 230 of locator tool 100 and used for the same purpose. The membrane 618 can also include various markings to facilitate alignment of the tool with an implanted valve. FIG. 2 shows a snowman shape drawn on the upper surface of the membrane 618, which can act as a reference for a physician or other operator. The membrane 618 also includes an arrow 620, which is similar to the arrow 220 of FIG. 1B, and lines 622, 624 similar to the lines 222, 224 of FIG. 1E. The elasticity, transparency, and thickness of the membrane 618 can also be similar to that discussed above with respect to the membrane 110 of FIGS. 1A-1E.

In use, a physician or other operator places the locator tool 600 on a patient's skin above an implanted valve. A lower surface of the membrane 618 can come into contact with the skin 216 above an underlying valve, depending on the degree of valve protrusion. The skin can be palpated through the membrane 618 and the position of the locator tool 600 adjusted accordingly so that the arrow 620 and the centerline CL are positioned above the valve, aligned with the axis of the valve. The membrane 218 will move by deforming toward the valve and/or around a skin protrusion above the valve. If desired, the skin can be marked through the hole 630. The indicator tool 104 and/or the adjustment tool 106 can then be placed on the upper surface of the membrane 618, and the annular ridge 634 can act as a hard stop to assist with providing a support to the indicator tool 104 and/or adjustment tool 106.

FIGS. 3A-3G illustrate another embodiment of a locator tool 700. In this embodiment, the tool 700 includes an annular base member 738 having a rigid deck 710 extending thereacross, a top cap 742 that mates to the base 738 and that includes markings for corresponding to a valve setting, a material or membrane 718 that is captured between the base member 738 and the top cap 742, and a ring 740 that is disposed around the base 738 and/or top cap 742 and that is mated to the membrane 718 for adjusting a tension of the membrane 718 across the tool.

Figure 3A:
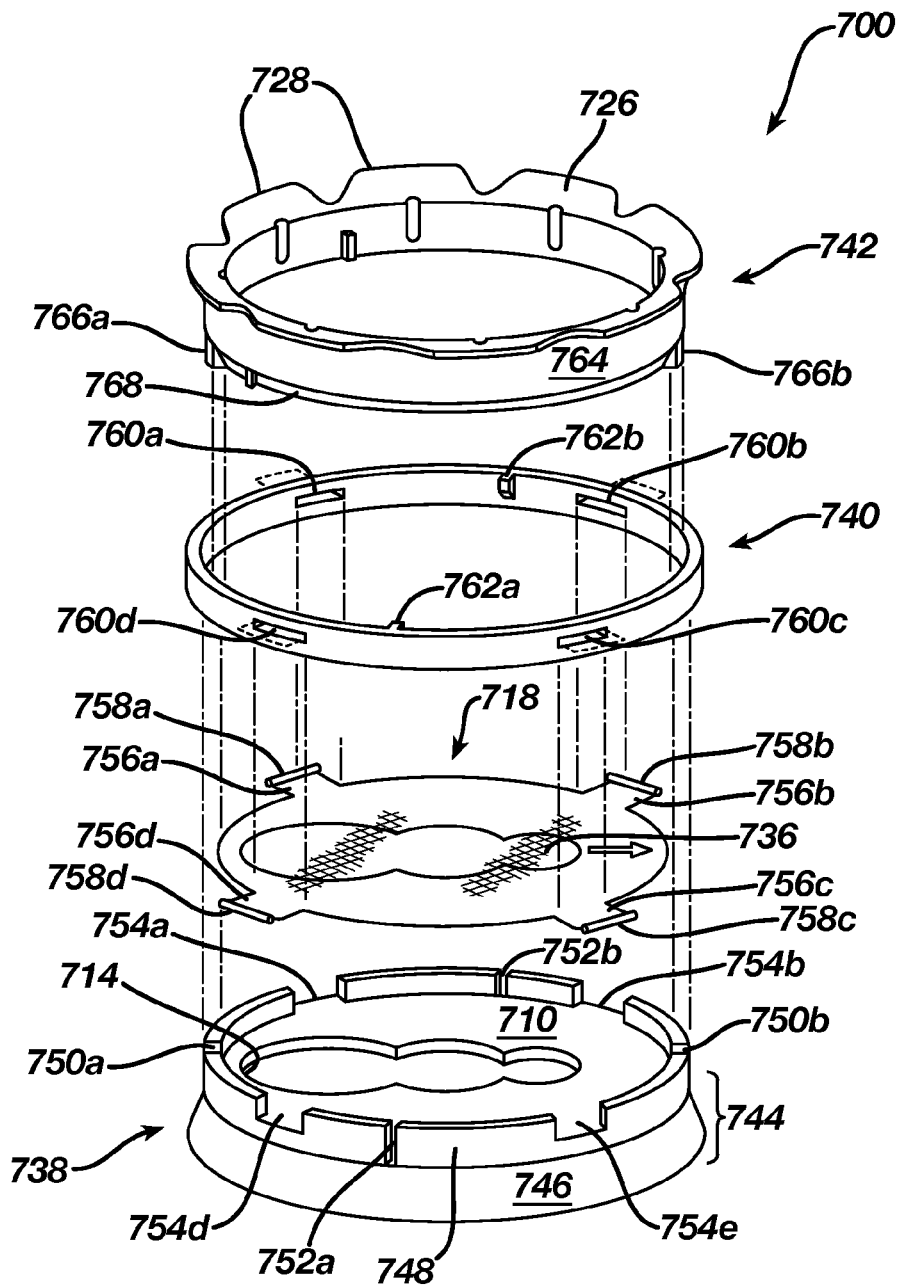
FIG. 3A is an exploded perspective view of another embodiment of a locator tool having an axially adjustable fabric membrane positioned above a rigid deck having a valve cut-out formed therein.

As best shown in FIG. 3A, the base member 738 includes an annular housing that is defined by a cylindrical wall 744. A lower portion 746 of the wall 744 can flare radially outward such that its diameter is greater at a distal end as compared to a proximal end of the lower portion 746. Such a configuration can provide additional stability when the base member 738 is seated on the skin of a patient. An upper portion 748 of the wall 744 can be substantially uniform in diameter.

The upper portion 748 of the wall 744 can include a number of slots 754a, 754b, 754c, 754d formed therein at its proximal-most end for receiving tabs formed on the membrane 718, as will be discussed below. The slots 754a-d can be spaced radially around the wall 744, although the spacing and the number of slots can vary. The wall 744 can also include one or more alignment slots 750a, 750b for facilitating alignment of the base member 738 with the top cap 742 and/or the ring 740, and optionally for mating the components. While only two alignment slots 750a-b are shown positioned on opposite sides of the wall 744 substantially in alignment with the centerline CL of the cut-out 714, the base member 738 can include any number of alignment slots formed therein and positioned at various locations. During assembly, the first pair of alignment slots 750a, 750b can be configured to align with corresponding protrusions 766a, 766b formed on a lower surface of the top cap 742. These slots 750a-b and protrusions 766a-b can be configured to lock the two components together, e.g., using an interference fit, snap-fit, or other mating connection. The wall 744 also includes a second pair of alignment slots 752a, 752b positioned on opposite sides of the wall 744, offset from the first pair of alignment slots 750a, 750b. The second pair of alignment slots 752a, 752b can be configured to receive corresponding protrusions 762a, 762b formed on an inner surface of the ring 740. The slots and protrusions not only facilitate alignment of the various components, but can also prevent rotation of the components relative to one another, thus maintaining proper rotational alignment of the components during use.

As further shown in FIG. 3A, the base member 738 also includes a deck 710 extending thereacross and occupying the opening defined by the wall 744. The deck 710 is in the form of a planar rigid portion and, similar to the rigid portion of the deck discussed above, includes a snowman-shaped cut-out 714 therein. The deck 710 can be positioned at various heights along the annular wall 744, but as shown the deck 710 sits approximately half-way up the wall 744 at a location between the upper portion 748 and the lower portion 746.

The top cap 742 can also be generally annular and it can be defined by a wall 764 which encloses an area of similar size to that enclosed by the upper portion 748 of the base member 738. Together the top cap 742 and the base member 738 can define the outer housing of the locator tool 700. The top cap 742 can include tabs 728 projecting outwards from the proximal-most end of the wall 764 to form a rim 726, similar to the rim 226 of FIGS. 1A-1E. The distal end of the wall 764 can include the deck locating protrusions 766a, 766b, which are dimensioned and located to correspond with respective deck locating alignment slots 750a-b in the base member 738, as discussed above. A recessed rim 768 can project downward from and extend around the bottom of the wall 764 for seating on the upper portion 748 of the base member 738.

The membrane 718, which is captured between the top cap 742 and the base member 738, can also have a variety of configurations and as shown is generally circular such that it occupies the opening defined by the top cap 742 and base member 738. The membrane 718 can form a part of the deck 710, in conjunction with the rigid portion. The membrane 718 can be transparent or opaque, or variations therebetween, and it can be formed from either an elastic or non-elastic material. In the illustrated embodiment, the is substantially non-elastic, but pliable to allow at least tactile access to the implanted valve. A snowman shaped marking 736 corresponding to the cut-out 714 in the deck 710 of the base member 738 may be disposed on the membrane 718.

The membrane 718 can also include four outwardly-protruding tabs 756a, 756b, 756c, 756d positioned to correspond with the respective tab slots 754a-d in the base member 738. The membrane 718 is sized such that the area of its circular portion corresponds to the area of the deck 710 when the tabs 756a-d are engaged with the deck locating slots 754a-d. The end of each tab 756 can include a respective retention bar 758a, 758b, 758c, 758d, which can be a cylindrical bar having a length that is greater than a width of the tab. Each bar 758a-d can be disposed through a sleeve created in the end of each tab. In use, the bars 758a-d will prevent the tabs 756a-d from passing back through the slots 754a-d in the base member 738, thereby retaining the membrane 718 within the base member 738.

The ring 740 is provided for allowing a tension of the membrane extending across the deck to be adjusted. The ring 740 can be generally dimensioned to fit snugly around the top cap 742 and base member 738, preferably at a substantial mid-portion thereof as shown in FIG. 3C. The ring 740 can include four thru-slots 760a, 760b, 760c, 760d extending through the wall of the ring 740, disposed at locations to correspond with respective tabs 756a-d and respective membrane tab slots 754a-d. The thru-slots 760a-d can be dimensioned such that the tabs 756a-d of the membrane 718 can pass through them but the membrane retention bars 758a-d cannot. The ring 740 can also include two ring locating tabs 762*a*, 762*b* which protrude towards the center of the ring 740 and which are dimensioned and located to correspond to respective ring locating slots 752*a*-*b*.

The four parts can be assembled as follows, although the order described could be varied. The membrane 718 is connected with the ring 740 by putting the tabs 756*a*-*d* through their respective slots 760*a*-*d*. The membrane retention bars 758*a*-*d* are then inserted into the sleeves at the ends of their respective tabs 756*a*-*d* to prevent the tabs from passing back through the slots 760*a*-*d*. Other methods of securing the membrane 718 to the ring 740 could be used, such as using adhesive or a mechanical grabber. The ring 740, together with the membrane 718 attached thereto, is placed over the base member 738, such that the tabs 756*a*-*d* are seated within their respective membrane tab slots 754*a*-*d*. Thus the membrane 718 is at least indirectly supported across the base member 738. The top cap 742 is placed within the ring 740 and over the membrane 718 such that the recessed rim 768 of its wall 764 sits on top of the upper portion 748 of the wall 744 of the base member 738, with the wall 764 and the upper portion 748 in alignment. The deck locating protrusions 766*a*-*b* are engaged in their respective deck locating slots 750*a*-*b*. This mating feature assists in holding the top cap 742 stably in place such that the whole is stably assembled.

Figure 3B:
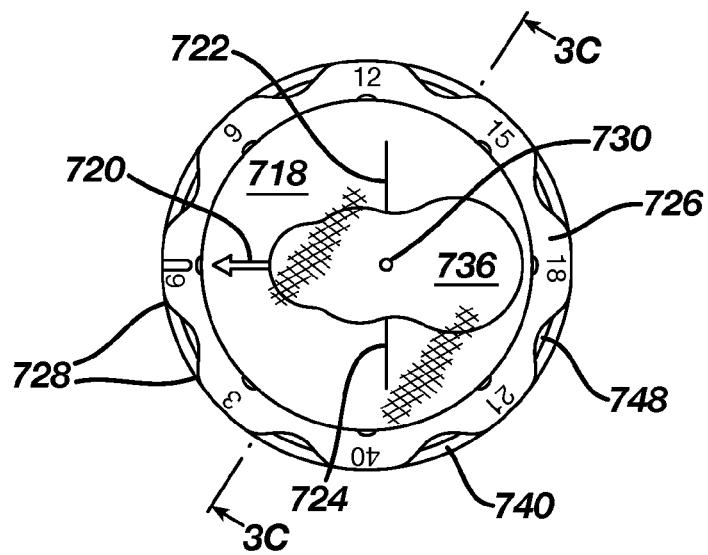
FIG. 3B is a top view of the device of FIG. 3A in the assembled configuration.
Figure 3C:
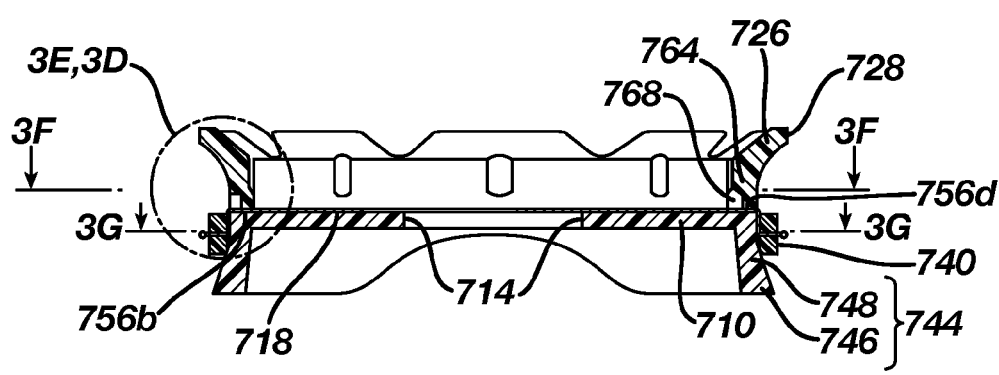
FIG. 3C is a side cross-sectional view of the device of FIG. 3B taken across line 3C.

FIG. 3B shows the arrangement of FIG. 3A, with the components assembled together as described above. It can be seen that the top surface of the membrane 718 forms a deck on which an indicator tool or an adjustment tool could be placed. The snowman-shaped marking 736 on the fabric of the membrane 718 is visible. An arrow 720, a center reference hole 730, and lines 722, 724 are also visible on the top of the membrane 718. Some portions of the ring 740 are visible between the tabs 728 of the rim 726 of the top cap 742. Some portions of the top of the upper portion 748 of the wall 744 of the base member 738 can be seen, indicating the annular surrounding of the wall 744 by the ring 740. FIG. 3C illustrates a cross-sectional view of the assembled locator tool 700, showing the membrane retaining tabs 756*b*, 756*d*. Each tab 756 is shown as being held between the bottom of the wall 764 of the top cap 742 and the top of the wall 744 of the base member 738.

Figure 3D:
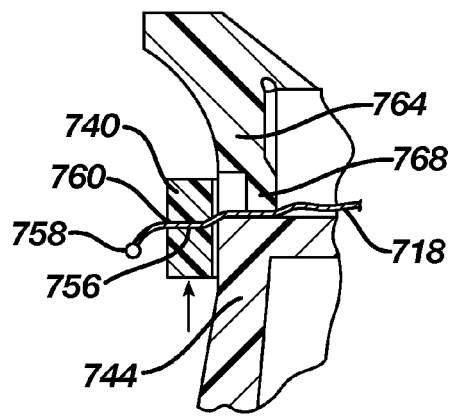
FIG. 3D is an enlarged side view of a mating connection of the locator tool shown in FIG. 3C, showing the fabric membrane in a tension-released configuration.
Figure 3E:
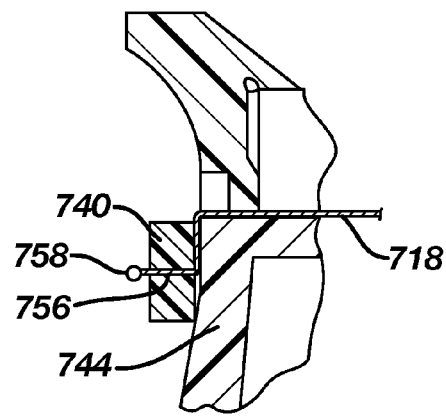
FIG. 3E is an enlarged side view of a mating connection of the locator tool shown in FIG. 3C, showing the fabric membrane in a tensioned configuration.

With the components fully assembly, the ring 740 can move proximally and distally along the central axis of the tool to adjust a tension of the membrane 718 extending across the opening of the tool 700. In particular, FIGS. 3D and 3E show a membrane retaining tab 756 in more detail. FIG. 3D shows the locator tool 700 with the membrane 718 in an untaut or loose configuration, and FIG. 3E shows the membrane 718 in a taut configuration. As shown, the ring is slid distally along the tool, e.g., toward a skin surface, to pull the membrane tab 756 distally, thereby applying tension to the membrane 718. Movement of the ring 740 in the opposite, proximal direction toward the plane containing the membrane 718 will release the tension applied to the membrane. In this embodiment, the ring 740 can be designed to frictionally engage an outer surface of the base member 738 so as to maintain the ring in a desired position. Alternatively, one or more locking features can be provided for maintaining the ring 740 in various positions. By way of non-limiting example, the ring 740 can include a protrusion formed on an inner surface thereof and the base member 738 can include a plurality of detents formed therein and positioned at various longitudinal positions (i.e., the detents can extend along a line running in a proximal-distal direction). The protrusion on the ring 740 can engage the detent to maintain the ring 740 in a desired position, thereby setting a tension of the membrane. A person skilled in the art will appreciate that a variety of other mechanisms can be used to allow the ring to be maintained in a desired position.

In use, the locator tool 700 is placed atop a valve implanted beneath skin. The valve may be palpated through the membrane 718 in the region of the cut-out 714 and the position of the locator tool 700 may be adjusted such that the cut-out 714 is aligned with the valve. The untaut nature of the membrane 718 allows the membrane 718 to move, which can assist a physician or other user in feeling the valve beneath the skin. In order to allow proper positioning of the indicator and adjustment tools within the locator tool 700, the membrane 718 can be moved to the taut configuration by pushing the ring 740 downwards towards the skin and thus further over the wall 744 of the base member 738. Since the membrane retention bars 758 prevent the membrane retaining tabs 756 from slipping out of the slots 760 of the ring 740, the membrane 718 is retained by the ring 740 and is consequently pulled more taut as the ring 740 moves further down the base member 738. The membrane 718 is shown in such a taut state in FIG. 3E.

Figure 3F:
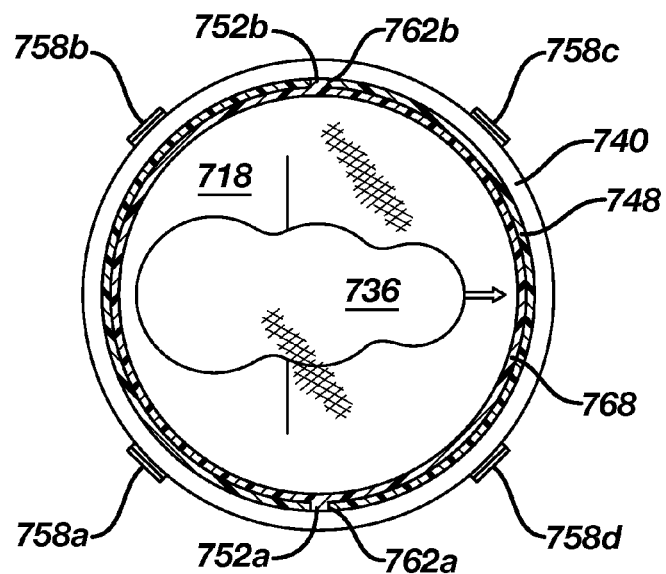
FIG. 3F is a top cross-sectional view of the locator tool of FIG. 3C taken across line 3F, with the fabric membrane in a tensioned configuration.
Figure 3G:
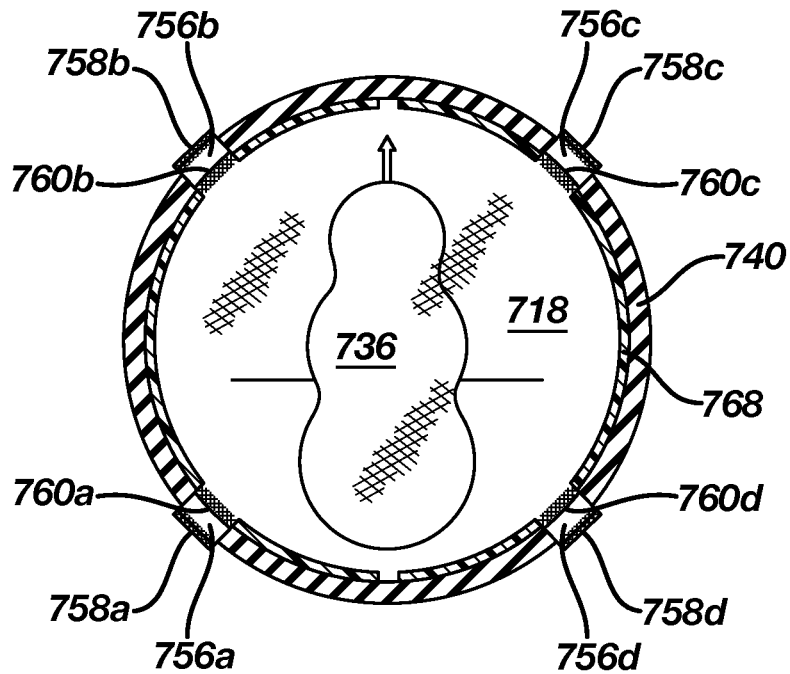
FIG. 3G is a top cross-sectional view of the locator tool of FIG. 3C taken across line 3G, with the fabric membrane in a tensioned configuration.

FIG. 3F shows a partial horizontal cross-section through the assembled locator tool 700, with the membrane 718 in a taut state. The deck locating protrusions 762*a*, 762*b* on the ring 740 can be seen as fitting snugly within their respective deck locating slots 752*a*, 752*b* on the base member 738. FIG. 3G also shows a partial horizontal cross-section through the assembled locator tool 700 with the membrane 718 in a taut state, but it is cut at a lower position than that of FIG. 3F. Specifically, it is cut through the slots 760*a*-*d* in the ring 740 at the membrane retaining tabs 756*a*-*d*. The membrane tabs change direction, i.e., extend horizontally outward and then turn and extend vertically in a distal direction. The change in direction occurs at a region of the membrane retaining tabs 756 which is sandwiched between the ring 740 and the upper portion 748 of the wall 744 of the base member 738.

It will be appreciated by those skilled in the art that alternative mechanical arrangements may be used instead of the adjustable ring 740 in order to move the membrane 718 between taut and untaut positions. An advantage of the ring is that it provides a uniform force around the membrane 718, thus minimizing the likelihood of twisting or otherwise deforming the fabric of the membrane 718. It will also be appreciated that a mechanism for locking the ring 740 in place could be provided. Moreover, the ring could move proximally rather than distally to apply tension to the membrane.

Figure 4:
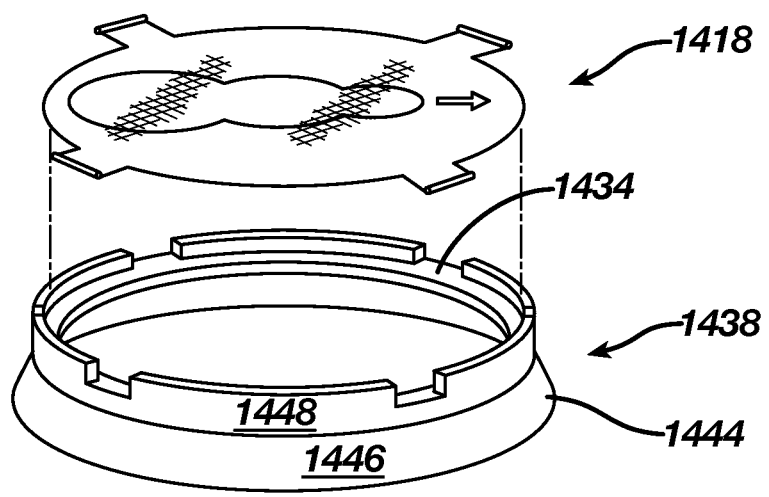
FIG. 4 is an exploded perspective view of another embodiment of a locator tool having a fabric membrane with markings formed thereon for locating an implanted valve.

While FIG. 3A illustrates a tool 700 having a deck that includes both a rigid portion having a valve cut-out and a membrane 718, in other embodiments the tool can have only a membrane without the rigid portion. FIG. 4 illustrates another embodiment of a base member 1438 and a membrane 1418 for use with the ring and top cap of FIGS. 3A-3G. The membrane 1418 is similar to the membrane 718 of FIGS. 3A-3G. The base member 1438 is similar to the base member 738 of 3A-3G in that it is formed of a wall 1444 which has an upper portion 1448 and a lower portion 1446, respectively similar to the upper portion 748 and lower portion 746 of the base member 738 of FIGS. 3A-3G. However, the base member 1438 differs from base member 738 in that instead of a deck such as the deck 710 of FIGS. 3A-3G, there is an annular ridge 1434, which is similar to the annular ridge 634 of FIG. 2. The annular ridge 1434 has an inner diameter which is slightly less than that of the upper portion 1448 of the wall 1444, thereby providing a ledge on which an outer circumference of the membrane 1418 can sit, and on which the adjustment and indicator tools can sit.

FIGS. 5A-5D illustrate another embodiment of a locator tool 1500 that is similar to the locator tool of FIG. 3A-3G but that includes a biasing element for biasing the membrane 1518 toward one of the taut and untaut configurations, and a locking mechanism for locking the ring 1540 when the membrane 1518 is in desired configurations. As shown, the top cap 1542 has a wall 1564, which is similar to the wall 764 of the implementations of FIGS. 3A-3G. The exterior of the wall 1564 includes a number of tubular members having bores extending therethrough. While only tubular members 1572c and 1572d are visible, it will be appreciated that the other two tubular members 1572a and 1572b are at the rear of the top cap 1542 in the view shown. The tubular members 1572 extend along substantially the full height of the wall 1564 and extend up at least partially into a rim 1526. In this example, there are four tubular members, each disposed to align close to a membrane retaining tab 1556, although the illustrated number and location of the tubular members is not essential.

The ring 1540 also includes correspondingly-located projections 1574a, 1574b, 1574c, 1574d which project from the upper surface of the ring 1540. There are also provided respective biasing members 1576a, 1576b, 1576c, 1576d, for example coil springs, which are sized to sit atop the projections 1574a-d such that each spring 1576a-d and at least a portion of each projection 1574a-d fit snugly within their respective tubular member 1572a-d.

The locator tool 1500 is assembled in a similar manner as described with respect to the locator tool 700 of FIGS. 3A-3G. The top cap 1542 is non-movably mated to the base 1538, e.g., by any mechanical mating technique, such as an adhesive, welding, fasteners, etc. When the top cap 1542 is mated to the base 1538, the tubular members 1572a-d are positioned to receive their respective springs 1576a-d and also to receive at least a portion of the length of a respective projection 1574a-d. All or a portion of the ring locating slots 752 and corresponding ring locators 762 of the embodiment of FIGS. 3A-3G can be omitted in the present embodiment because the tubular members 1572a-d, together with the projections 1574a-d, can function as locators as well as a locking mechanism.

Figure 5A:
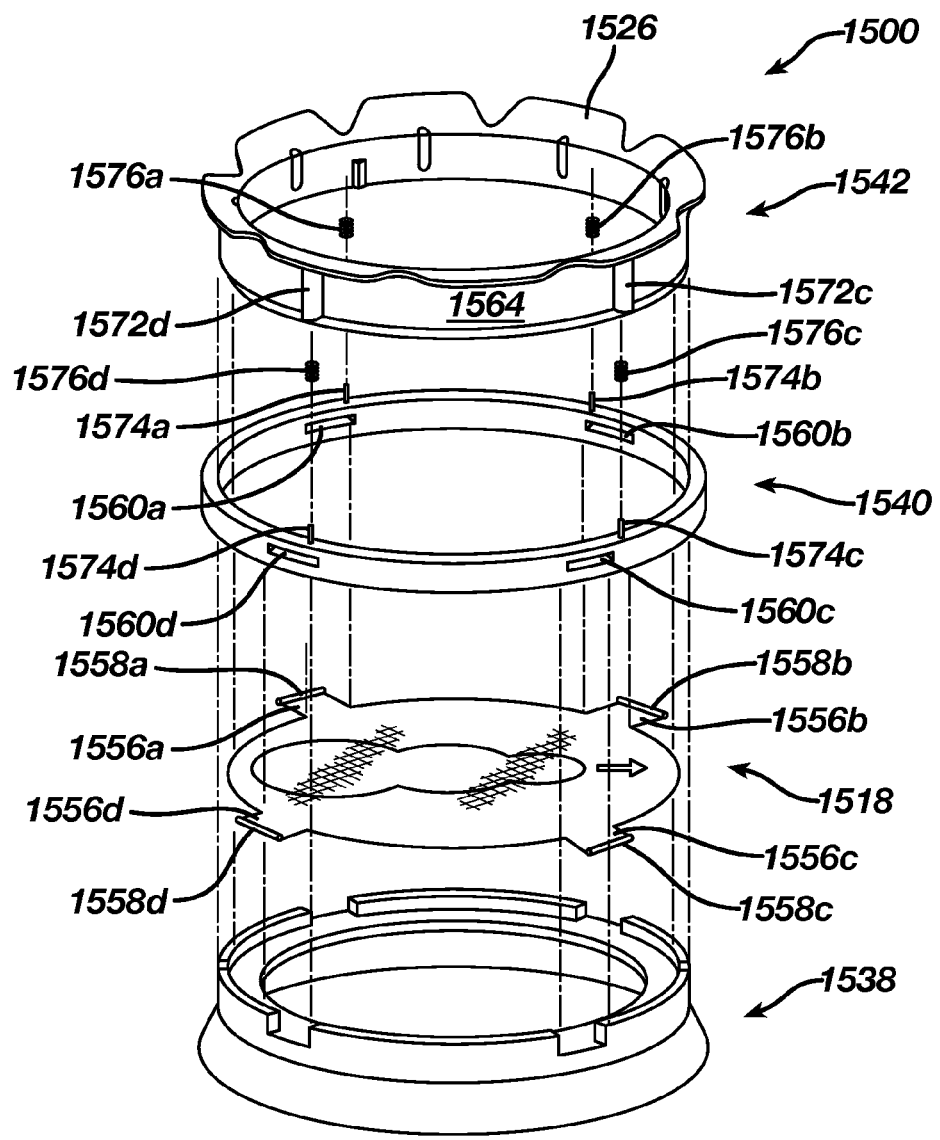
FIG. 5A is an exploded perspective view of yet another embodiment of a locator tool that is similar to the embodiment of FIG. 3A, but that includes a biasing element for biasing the fabric membrane toward a desired axial position.

FIG. 5B shows the locator tool of FIG. 5A in an assembled configuration. The same two tubular members 1572c, 1572d are visible in this figure. Their corresponding projections 1574c, 1574d and first springs 1576c, 1576d are not visible because in this configuration they are enclosed within their respective tubular members. The membrane 1518 is held across the ring 1540 and two of the membrane retention bars 155+8c, 1558d can be seen as holding the membrane 1518 in place by preventing the tabs 1556c, 1556d from retracting through the slots 1560c, 1560d. Further components of the locking mechanism will now be described.

FIG. 5C shows the locator tool with the membrane 1518 in an untaut configuration and the ring 1540 in a first, initial position. In this configuration, the spring 1576d is compressed within the tubular member 1572d by the projection 1574d. A majority of the length of the projection 1574d is held within the tubular member 1572d, with the remainder being visible in a space between the wall 1564 of the top cap 1542 and the base member 1538, with a lowermost portion being integrally formed on or fixedly mated to and held within a recess in the top face of the ring 1540. The projection 1574d includes three detents 1578d, 1580d, 1582d formed thereon and arranged in a descending manner, and the detents 1578d, 1580d, 1582d are disposed within the tubular member 1572d of the top cap 1542. The detents interact with a second spring 1584d, disposed at approximately 90° to the first spring 1576d such that the second spring can co-operate with the detents 1578d, 1580d, 1582d to maintain the ring 1540 in a set position. In the configuration of FIG. 5C, the second spring 1584d is engaged with the distal-most detent 1582d to maintain the ring in a proximal-most position such that the membrane 1518 is untaut. As a result, the ring 1540 overcomes the biasing force of the spring 1576d and causes the spring 1576d to fully compress. It will be appreciated that the other tubular members 1572, first springs 1576, second springs 1584, first detents 1578, and projections 1574 can interact in a similar manner and may do so substantially simultaneously, providing that the ring 1540 is placed evenly over the wall 1564 of the base member 1538. The locator tool 1500 may be provided to a physician or other operator in this configuration, and the operator may then place the locator tool on the skin of a patient and adjust its location and/or orientation by palpating the valve through the membrane 1518, in a similar manner as described with respect to previous exemplary implementations. The untaut nature of the membrane 1538 will allow the membrane to move to allow palpation of the underlying valve.

In order to apply tension to the membrane 1518 to move it to a taught configuration for seating the adjustment and indicator tools, an operator can selectively exert a force e.g. by pushing distally on the ring 1540. The force can be generally perpendicular to the membrane and toward the patient's skin, as shown by arrow F. As the ring 1540 is advanced along the top cap 1542 and toward and along the base 1538, the first spring 1576d facilitates movement by applying a distally-directed forward to the projection 1574d. In response to a first force, the ring 1540 moves downwards, thereby causing the distal-most detent 1582d to disengage from the second spring 1584d and causing the middle detent 1580d to engage with the second spring 1584d. It may be decided that the membrane 1518 is sufficiently taut at this stage. If it is desired to make it more taut, a further, second force can be selectively exerted on the ring 1540, causing the spring 1572d to be further uncompressed and causing the middle detent 1580d to disengage from the second spring 1584d and causing the proximal-most detent 1578d to engage with the second spring 1584d. An exemplary cross-section through tubular member 1572d is shown with the components in this position in FIG. 5D. It can be seen that in this configuration, a majority of the projection 1574d is removed from the tubular member 1572d. When any of the detents 1578d, 1580d, 1582d is engaged with a second spring 1584d, the ring 1540 can be disengaged by exerting a proximal force on the ring to compress the spring and move the membrane back to the untaut configuration. It will be appreciated that the other tubular members 1572, first springs 1576, second springs 1584, first detents 1578, and projections 1574 can interact in a similar manner and may do so substantially simultaneously, providing that the ring 1540 is placed evenly over the wall 1564 of the base member 1538.

The arrangement of tubular members 1572, detents 1578, 1580, 1582, first springs 1576, second springs 1584, and projections 1574 allows the locator tool 700 to be locked with the membrane 1518 having a desired tautness. While the illustrated embodiment shows three membrane positions having differing states of tautness, a person skilled in the art will appreciate that the membrane 1518 can have any number of positions. Moreover, the device can be configured such that movement of the ring in a proximal direction, rather than a distal direction, causes a tension applied to the membrane to increase. The device can further be configured such that the ring is biased to the untaut configuration, rather than biased to the distal-most taut configuration as shown in the FIG. 5D.

It will be understood by those skilled in the art that the specific locking mechanism described could be varied and that the precise arrangement of components is not essential. For example, more or fewer locking mechanisms could be provided, with optionally some simple projections and guide recesses at other locations around the locator tool 700. Other exemplary variations include the number of detents and the type of biasing member. For example, a leaf spring could be used. The described locking mechanism and other locking mechanisms could be used together with the implementation of FIGS. 1A-4.

Moreover, while the membranes of FIGS. 3A-5D are illustrated as having four tabs to facilitate holding of the membrane in place, other configurations are possible. For example, more or fewer tabs could be provided, for example three, five, six or more tabs. Another optional variation would be to provide a tab around the extent of the membrane and use such a continuous tab to hold the membrane to the ring, for example by adhesive or other welding means or a mechanical grabber mechanism.

A person skilled in the art will appreciate that, while the locator tool shown in FIGS. 5A-5D has only a membrane 1518 that forms the deck, the locator tool can include a rigid portion having a valve cut-out. The rigid portion may or may not be present in any of the embodiments herein. A person skilled in the art will also appreciate that the membrane in any of the embodiments disclosed herein can be elastic or non-elastic, transparent or opaque, or any combination thereof. Each of the embodiments disclosed herein can include features to allow a height of the deck to be adjusted, as disclosed in co-pending U.S. application Ser. No. 14/040, 865. In such a configuration, a moveable platform would be provided on which the deck and/or membrane are supported. For example, the exemplary decks and/or ridges described above could be adjustable. However, the exemplary membranes may provide sufficient adjustability that no further mechanical adjustment is required. A person skilled in the art will further appreciate that any of the embodiments disclosed herein can include features to allow a tension of the membrane to be adjusted, e.g., using a sliding ring or other adjustment mechanism.

Figure 6:
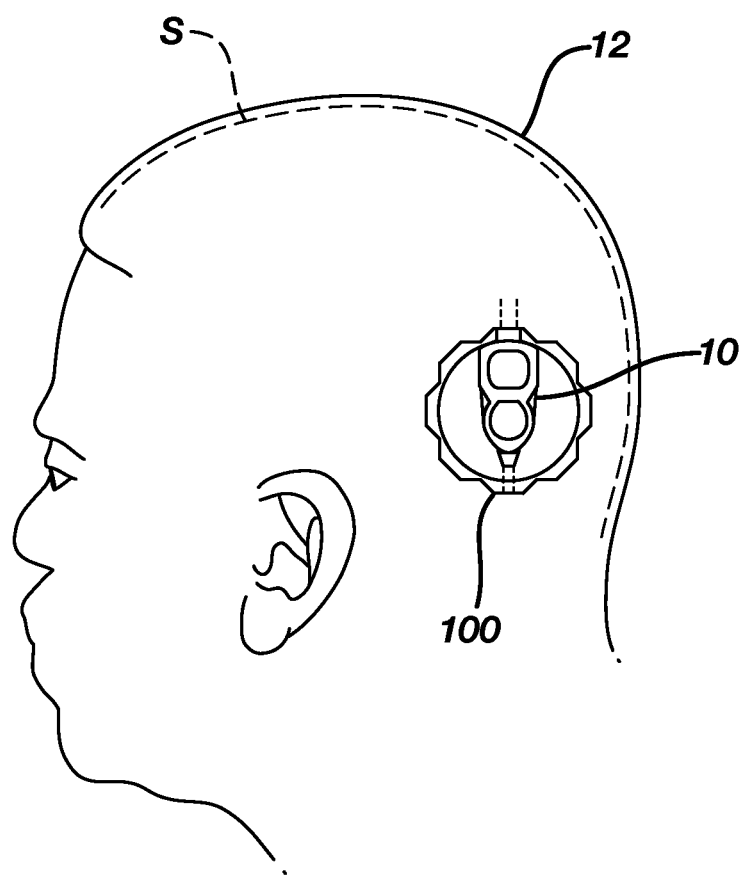
FIG. 6 shows the locator tool of FIG. 1A positioned on a patient's scalp for locating a valve implanted beneath a skin surface of the patient's scalp.

The various embodiments of locator tools disclosed herein can be used to read and/or adjust the setting of an implantable valve. Such a method can include, with reference to FIG. 6, positioning the locator tool 100 in alignment over a valve, and placing an indicator tool 104 (FIG. 1A) on the deck of the locator tool 100 such that it is seated in the locator tool 100. The indicator tool 104 can have a compass which is configured to align with the magnet in the valve, to thereby indicate the current setting of the valve. The indicator tool 104 can a visual indicator of the setting. Once the current valve setting has been determined, the indicator tool 104 can be removed and the adjustment tool 106 can be seated in the locator tool 100 and used to adjust the setting of the valve. The adjustment tool 106 can have a magnet which is able to engage with the magnet of the valve and thus the magnet of the valve can be manipulated by rotating the adjustment tool relative to the locator tool, thereby moving the magnet.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A locator tool for locating a valve implanted beneath skin, comprising:
    an annular base member having a proximal end and a distal end that is configured to be placed on a skin surface above a valve implanted beneath the skin surface; and
    a deck supported across the base member and having at least a portion formed of a material through which at least one of visual and tactile access is obtainable, the material being movable to accommodate a valve protrusion in a skin surface on which the base member is configured to be placed, wherein the material comprises an elastic material which is movable deforming around a protrusion of skin.

2. The tool of claim 1, wherein at least a portion of the material is transparent to allow a valve to be seen therethrough.

3. The tool of claim 1, wherein the material includes one or more holes for marking at least one of a location and an orientation of a valve.

4. The tool of claim 1, wherein the base member has a central opening extending therethrough and defining a central axis, and wherein the material is held by an annular support member mounted to move relative to the base member along the central axis.

5. The tool of claim 4, wherein the base member and the annular support member include corresponding slots and protrusions to allow relative movement between the base member and the support member.

6. The tool of claim 4, further comprising a mechanism to selectively fix the support member relative to the base member.

7. The tool of claim 4, further comprising a biasing element for biasing the support member toward a proximal end of the base member.

8. A locator tool for locating a valve implanted beneath skin, comprising:
    an annular base member having a proximal end and a distal end that is configured to be placed on a skin surface above a valve implanted beneath the skin surface; and
    a deck supported across the base member and having at least a portion formed of a material through which at least one of visual and tactile access is obtainable, the material being movable to accommodate a valve protrusion in a skin surface on which the base member is configured to be placed, wherein the deck includes a rigid portion extending across the base member and having a valve cut-out formed therein, the material extending across the valve cut-out.

9. The tool of claim 8, wherein the material is movable toward and away from the rigid portion.

10. The tool of claim 8, wherein the material of the deck comprises a non-elastic material.

11. A locator tool for locating a valve implanted beneath skin, comprising:
    an annular base member having a proximal end and a distal end that is configured to be placed on a skin surface above a valve implanted beneath the skin surface; and
    a deck supported across the base member and having at least a portion formed of a material through which at least one of visual and tactile access is obtainable the material being movable to accommodate a valve protrusion in a skin surface on which the base member is configured to be placed, wherein the material of the deck comprises a non-elastic material, and wherein the non-elastic material is movable between a taut configuration and an untaut configuration in which the material can move around a protrusion of skin.

12. The tool of claim 8, wherein the material comprises an elastic material which is movable by deforming around a protrusion of skin.

13. The tool of claim 11, further comprising an adjustment mechanism for adjusting a tautness of the material.

14. A kit for locating and adjusting a valve implanted beneath a skin surface, comprising:
    a locator tool having
        an annular base member configured to be placed on a skin surface above a valve implanted beneath the skin surface, and
        a deck supported across the base member and having at least a portion formed of a material through which at least one of visual and tactile access is obtainable, the material being movable to accommodate a valve protrusion in a skin surface on which the base member is configured to be placed, wherein the deck includes a rigid portion having a valve cut-out formed therein, and wherein the material extends across the valve cut-out;
    an indicator tool removably disposable within the locator tool and configured to indicate a setting of a valve; and
    an adjustment tool removably disposable within the locator tool and configured to adjust a setting of a valve.

15. The kit of claim 14, wherein at least a portion of the deck of the locator tool forms a platform on which the indicator tool and the adjustment tool seat against when disposed therein.

16. A method of locating a valve implanted beneath skin, comprising:
    positioning a base member of a locator tool on a skin surface above a valve implanted beneath the skin surface, at least a portion of a deck of the locator tool supported across the base member moving relative to the base member to accommodate a protrusion of skin around the valve.

17. The method of claim 16, wherein the at least a portion of the deck comprises a material that moves relative to the base member to accommodate a protrusion of skin around the valve, and the method further comprises adjusting a height of the material relative to the base member and the skin surface.

18. The method of claim 16, wherein the at least a portion of the deck comprises a material that moves relative to the base member to accommodate a protrusion of skin around the valve, and the method further comprises moving the material from an untaut position to a taught position.

19. The method of claim 16, further comprising marking skin beneath the deck through holes in the deck to indicate features of a valve.

20. The method of claim 16, further comprising selectively placing at least one of an indicator and a valve adjustment tool on the deck.

* * * * *